US010779886B2

(12) United States Patent
Buttar et al.

(10) Patent No.: US 10,779,886 B2
(45) Date of Patent: Sep. 22, 2020

(54) THERMAL THERAPY SYSTEMS AND METHODS

(71) Applicant: Mayo Foundation for Medical Education and Research, Rochester, MN (US)

(72) Inventors: Navtej S. Buttar, Rochester, MN (US); Louis-Michel Wong Kee Song, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 352 days.

(21) Appl. No.: 15/547,637

(22) PCT Filed: Jan. 26, 2016

(86) PCT No.: PCT/US2016/014903
§ 371 (c)(1),
(2) Date: Jul. 31, 2017

(87) PCT Pub. No.: WO2016/126461
PCT Pub. Date: Aug. 11, 2016

(65) Prior Publication Data
US 2018/0147009 A1 May 31, 2018

Related U.S. Application Data

(60) Provisional application No. 62/111,238, filed on Feb. 3, 2015.

(51) Int. Cl.
*A61B 18/18* (2006.01)
*A61B 1/00* (2006.01)
(Continued)

(52) U.S. Cl.
CPC ...... *A61B 18/1815* (2013.01); *A61B 1/00087* (2013.01); *A61B 1/00089* (2013.01);
(Continued)

(58) Field of Classification Search
CPC ............ A61B 1/00087; A61B 1/00101; A61B 1/00131; A61B 1/00137; A61B 2017/00296; A61B 2018/1495
See application file for complete search history.

(56) References Cited

U.S. PATENT DOCUMENTS 5,593,405 A * 1/1997 Osypka .............. A61B 1/00082
606/15
6,086,583 A * 7/2000 Ouchi ................ A61B 1/00089
604/35
(Continued)

OTHER PUBLICATIONS

Extended European Search Report in Euroupean Application No. 16746979.0 dated Oct. 8, 2018, 45 pages.
(Continued)

*Primary Examiner* — Laura A Bouchelle
(74) *Attorney, Agent, or Firm* — Fish & Richardson P.C.

(57) ABSTRACT

Devices and methods can be used to deliver thermal therapy to treat tissue. For example, this document provides devices and methods for treating varices, varicosity, other bleeding vessels, polyps, and cancer using microwave-delivered thermal therapy in a minimally invasive fashion. In some embodiment's provided herein, a multidirectional thermal therapy that does not injure surface tissues but causes endothelial injury and coagulation is described. In some implementations, varices are suctioned into a cup that is configured to deliver thermal therapy to the varices, resulting in coagulation.

9 Claims, 7 Drawing Sheets

(51) Int. Cl.
*A61B 1/015* (2006.01)
*A61N 5/02* (2006.01)
*A61B 18/00* (2006.01)

(52) U.S. Cl.
CPC .............. *A61B 1/015* (2013.01); *A61N 5/022* (2013.01); *A61B 2018/00023* (2013.01); *A61B 2018/00029* (2013.01); *A61B 2018/0072* (2013.01); *A61B 2018/00404* (2013.01); *A61B 2018/00482* (2013.01); *A61B 2018/00488* (2013.01); *A61B 2018/00577* (2013.01); *A61B 2018/00589* (2013.01); *A61B 2018/00642* (2013.01); *A61B 2018/00702* (2013.01); *A61B 2018/00726* (2013.01); *A61B 2018/00785* (2013.01); *A61B 2018/00791* (2013.01); *A61B 2018/00797* (2013.01); *A61B 2018/00815* (2013.01); *A61B 2018/00821* (2013.01); *A61B 2018/00863* (2013.01); *A61B 2018/00875* (2013.01); *A61B 2018/1861* (2013.01); *A61B 2218/002* (2013.01); *A61B 2218/007* (2013.01)

(56) References Cited

U.S. PATENT DOCUMENTS

| | | | |
|---|---|---|---|
| 6,106,521 A * | 8/2000 | Blewett | A61B 18/1477 600/105 |
| 6,544,226 B1 | 4/2003 | Gaiser et al. | |
| 7,303,561 B2 * | 12/2007 | Ouchi | A61B 1/00089 606/45 |
| 2007/0016274 A1 | 1/2007 | Boveja et al. | |
| 2010/0256632 A1 | 10/2010 | Crowley et al. | |
| 2013/0046138 A1 | 2/2013 | McLawhorn | |
| 2013/0046300 A1 * | 2/2013 | Binmoeller | A61B 18/1492 606/41 |
| 2014/0012247 A1 | 1/2014 | Bakos et al. | |

OTHER PUBLICATIONS

Baldaque-Silva et al., "Radiofrequency ablation for the treatment of gastric dysplasia: a pilot experience in three patients," *Eur J Gastroenterol Hepatol.*, 25(7):863-868, Jul. 2013.

Dietzek., "Endovenous radiofrequency ablation for the treatment of varicose veins," *Vascular.*, 15(5):255-261, Sep.-Oct. 2007.

International Preliminary Report on Patentability in International Application No. PCT/US2016/014903, dated Aug. 8, 2017, 7 pages.

International Search Report and Written Opinion in International Application No. PCT/US2016/014903, dated Mar. 31, 2016, 9 pages.

Jacobsen et al., "Dual-mode antenna design for microwave heating and noninvasive thermometry of superficial tissue disease," *IEEE Transactions on Biomedical Engineering.*, 47(11):1500-1509, Nov. 2000.

Saito et al., "Practical evaluations on heating characteristics of thin microwave antenna for intracavitary thermal therapy," *Conf Proc IEEE Eng Med Biol Soc.*, 2010:2755-2758, 2010.

Van-Vilsteren et al., "Radiofrequency ablation for the endoscopic eradication of esophageal squamous high grade intraepithelial neoplasia and mucosal squamous cell carcinoma," *Endoscopy.*, 43:282-290, 2011.

* cited by examiner

THERMAL THERAPY SYSTEMS AND METHODS

CROSS REFERENCE TO RELATED APPLICATIONS

This application is a National Stage application under 35 U.S.C. § 371 of International Application No. PCT/US2016/014903, having an International Filing Date of Jan. 26, 2016, which claims the benefit of U.S. Provisional Application No. 61/111,238, filed Feb. 3, 2015. The disclosure of the prior applications are considered part of and are incorporated by reference in the disclosure of this application.

BACKGROUND

1. Technical Field

This document relates to devices and methods for delivering thermal therapy. For example, this document relates to devices and methods for treating conditions including varices, varicosity, hemorrhoids, polyps, cancer, and for controlling bleeds in the GI tract, using microwave-delivered thermal therapy in a minimally invasive fashion.

2. Background Information

Esophageal varices are abnormal, enlarged veins in the lower part of the esophagus—the tube that connects the throat and stomach. Esophageal varices occur most often in people with serious liver diseases, such as cirrhosis. Esophageal varices develop when normal blood flow to the liver is obstructed by scar tissue in the liver or a clot. Seeking a way around the blockages, blood flows into smaller blood vessels that are not designed to carry large volumes of blood. The vessels may leak blood or even rupture, causing life-threatening bleeding.

The exact prevalence of cirrhosis worldwide is unknown. Cirrhosis prevalence is estimated at 0.15% or 400,000 patients in the USA, where it accounted for more than 25,000 deaths and 373,000 hospital discharges. This may be an underestimation as we recognize the high prevalence of undiagnosed cirrhosis in both NASH and hepatitis C. Similar numbers are reported from Europe, and numbers are even higher in most Asian and African countries where chronic viral hepatitis B or C are frequent.

Approximately 50% to 80% of patients with cirrhosis develop varices in the esophagus or stomach. Up to 25% of these patients will have large varices that could bleed with high mortality and morbidity (up to 20-40%). The current treatment options such as medications or band ligation are either poorly tolerated or could result in ulceration due to mechanical trauma.

SUMMARY

This document provides devices and methods for delivering thermal therapy. For example, this document provides devices and methods for treating conditions such as, but not limited to, varices, varicosity, other bleeding vessels, polyps, hemorrhoids, cancer, Barret's oesophagus, EMR, ESD, haemostasis, and for controlling bleeds in the GI tract using microwave-delivered thermal therapy in a minimally invasive fashion.

In some embodiments provided herein, a multidirectional thermal therapy that does not injure surface tissues but causes endothelial injury and coagulation is described. In some implementations, varices are suctioned into a cup that is configured to deliver thermal therapy to the varices, resulting in coagulation. In some such embodiments, an endoscopic device with cap-incorporated microwave delivery elements (axial or peripheral), with or without Doppler modulation of microwave energy, can direct heat in submucosal tissue to cause rapid coagulation and eventual obliteration of varices without surface injury. Surface cooling via endoscope cap ports or using an auxiliary cooling media supply, may optionally be included to further reduce the potential of surface injury.

In one implementation, an apparatus for minimally invasive delivery of therapeutic energy to a target area of a patient includes a cap assembly that is configured to be releasably coupled to a distal end portion of an endoscope, an energy source, and at least one energy delivery element. The at least one energy delivery element is coupled to the cap assembly and configured to receive energy from the energy source and to deliver the energy to the target area.

Such an apparatus for minimally invasive delivery of therapeutic energy to a target area of a patient may optionally include one or more of the following features. The at least one energy delivery element may be releasably coupled to the cap assembly. The energy source may be a microwave energy source. The microwave energy source may be configured to deliver microwave energy on a pulsatile basis. The apparatus may further comprise a temperature sensor that is configured to detect a temperature of the target area and to provide a signal indicative of the temperature to the energy source. The at least one energy delivery element may comprise two energy delivery elements.

In another implementation, a system for minimally invasive delivery of therapeutic energy to a target area of a patient includes an endoscope, a cap assembly that is releasably coupleable to a distal end portion of the endoscope, an energy source, and at least one energy delivery element. The at least one energy delivery element is coupled to the cap assembly. The at least one energy delivery element is configured to receive energy from the energy source and to deliver the energy to the target area.

Such a system for minimally invasive delivery of therapeutic energy to a target area of a patient may optionally include one or more of the following features. The at least one energy delivery element may be releasably coupled to the cap assembly. The energy source may be a microwave energy source. The microwave energy source may be configured to deliver microwave energy on a pulsatile basis. The system may further comprise a temperature sensor configured to detect a temperature of the target area, and to provide a signal indicative of the temperature to the energy source. The at least one energy delivery element may comprise two energy delivery elements. The endoscope may be configured to deliver suction to the target area. The endoscope may be configured to deliver an irrigation fluid to the target area.

In another implementation, a method for minimally invasive delivery of therapeutic energy to a target area of a patient includes navigating a distal end portion of an endoscope to the target area, and energizing the at least one energy delivery element with energy from the energy source. The energizing directs the therapeutic energy to the target area. The distal end portion has a cap assembly releasably coupled thereto. The cap assembly has at least one energy delivery element coupled thereto. The at least one energy delivery element is configured and operable to receive energy from an energy source and to deliver the energy to the target area.

Such a method for minimally invasive delivery of therapeutic energy to a target area of a patient may optionally include one or more of the following features. The method may further comprise suctioning at least a portion of the target area into an interior space defined by the cap assembly. The target area may comprise a blood vessel, and the energizing may result in coagulation of blood within the blood vessel. In some implementations, the blood vessel is an esophageal varix. The method may further comprise delivering an irrigation fluid to the target area through a channel of the endoscope or via an auxiliary supply coupled to the endoscope. The energy source may be a microwave energy source, and the microwave energy source may be configured to deliver microwave energy on a pulsatile, pattern, or otherwise inconsistent basis. The method may further comprise delivering a chemical or biological agent through the distal end portion of the endoscope. The energizing may change the chemical or biological agent. The method may further comprise using a cryoenergy agent to facilitate adherence of the distal end portion of the endoscope to the target area. The at least one energy delivery element may comprise at least two energy deliver elements. The energy source may be a microwave energy source that is configured to deliver microwave energy on a phasic microwave energy delivery basis from the at least two energy deliver elements. The method may further comprise modulating the therapeutic energy during the energizing based on measured impedance, temperature, or blood flow. The therapeutic energy may comprise a type of high-frequency electromagnetic energy other than microwaves.

Particular embodiments of the subject matter described in this document can be implemented to realize one or more of the following advantages. In some embodiments, esophageal varices can be treated using the devices and methods provided herein. Such treatments can be advantageously delivered perorally using a retractable endoscopic, catheter, or probe-based solution for coagulating and treating esophageal varices. The thermal energy can be delivered so that epithelial damage and coagulation result, while not inflicting substantial surface tissue damage. In some embodiments, the treatment can be delivered in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 5 shows a perspective view of a distal tip portion of an endoscope that is configured with a cap and microwave energy delivery elements, and that includes an auxiliary channel for delivery of suction, irrigation, energy, and the like.

FIG. 6 shows a perspective view of another distal tip portion of an endoscope that is configured with a cap and microwave energy delivery elements, and that includes an auxiliary channel for delivery of suction, irrigation, energy, and the like.

Like reference numbers represent corresponding parts throughout.

DETAILED DESCRIPTION

This document provides devices and methods for delivering thermal therapy. For example, this document provides devices and methods for treating varices and/or cancer using microwave-delivered thermal therapy in a minimally invasive fashion. One who is skilled in the relevant art will appreciate that the devices, systems, and methods provided herein also have other beneficial applications. For example, health conditions such as, but not limited to, gastric varices, hemorrhoids, varicose veins, cancer, and cardiac tumors, and others can be treated using the systems and methods provided herein.

Figure 1:
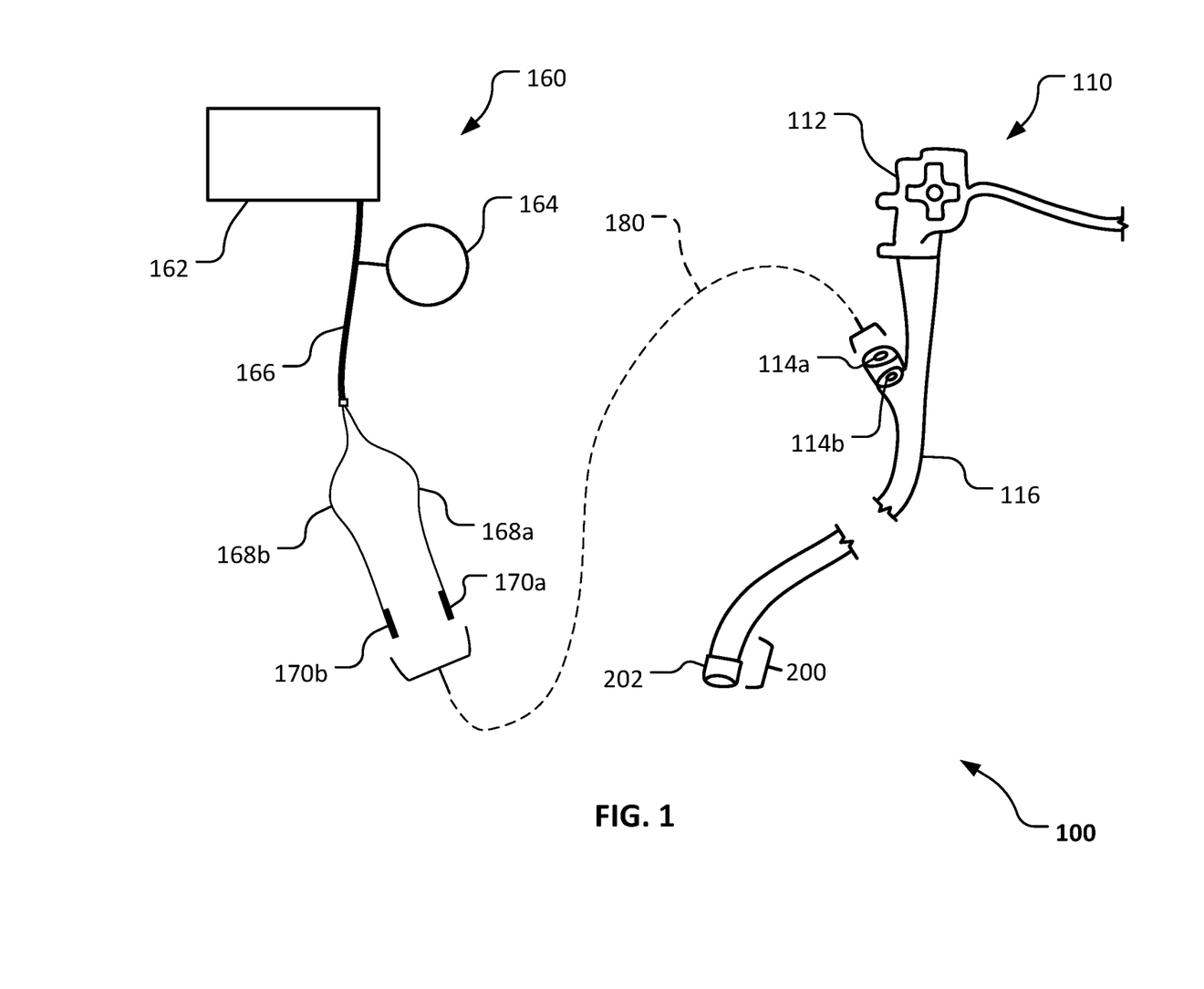
FIG. 1 is a schematic diagram of a system for endoscopically treating varices, varicosity, other bleeding vessels, polyps, and/or cancer using microwave-delivered thermal therapy, in accordance with some embodiments provided herein.

With reference to FIG. 1, an example system 100 for providing thermal therapy includes an endoscope apparatus 110 and a microwave energy system 160. As depicted by dashed line 180, endoscope apparatus 110 and microwave energy system 160 are configured to be releasably conjoined with each other in an arrangement whereby microwave energy can be endoscopically delivered to a target area internal to a patient.

While the depicted example system 100 depicts a microwave energy system 160, it should be understood that other types of high-frequency electromagnetic radiation energy may additionally or alternatively be used. For example, types of electromagnetic radiation energy such as, but not limited to infrared, ultraviolet, X-rays, gamma rays, and the like can be used as a type of electromagnetic energy for example system 100.

Endoscope apparatus 110 includes a control handle 112, a first channel 114a, a second channel 114b, an endoscope shaft 116, and a cap assembly 202. Cap assembly 202 is releasably coupled to shaft 116 at a distal end portion 200 of shaft 116. Endoscope apparatus 110 is a standard and commonly known device. It should be understood, therefore, that cap assembly 202 is configured to be releasably coupleable to a standard endoscope shaft 116. As such, cap assembly 202 is scalable in a variety of sizes that are proportionate to various sizes of endoscope shafts 116.

While the depicted embodiment of endoscope apparatus 110 includes two channels 114a and 114b, in some embodiments of endoscope apparatus 110 only a single channel is included. It should be understood that single port endoscope apparatuses can be used as a part of system 100 as well as the dual port endoscope apparatus 110 shown. In some embodiments, three or more channels may be included in the endoscope apparatus that is used as a part of system 100.

In some embodiments, endoscope apparatus 110 can deliver suction to cap assembly 202. Hence, in some embodiments cap assembly 202 can function as a suction cup. The vacuum for suction may be supplied via the endoscope apparatus 110 or through a channel that is auxiliary to the endoscope apparatus 110 (e.g., see auxiliary channel 310 shown in FIG. 5, and auxiliary channel 410 shown in FIG. 6). However, in some embodiments no suction is included. In some embodiments, endoscope apparatus 110 can deliver an irrigation fluid. The irrigation fluid may be supplied via the endoscope 110 or through a channel that is auxiliary to the endoscope 110 (e.g., auxiliary channels 310 or 410). Such an irrigation fluid can provide a cooling affect that may reduce the potential of inflicting surface tissue damage when treatment energy is delivered to the target site internal to the patient.

Figure 5:
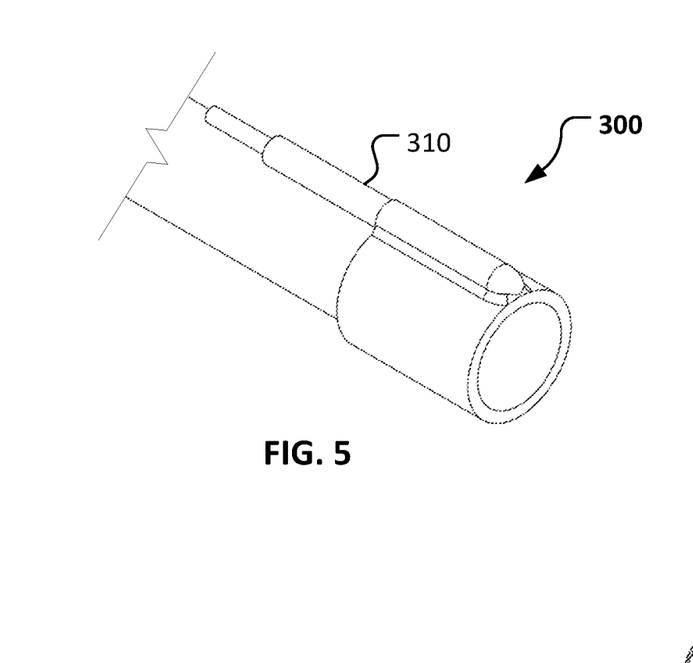
Figure 6:
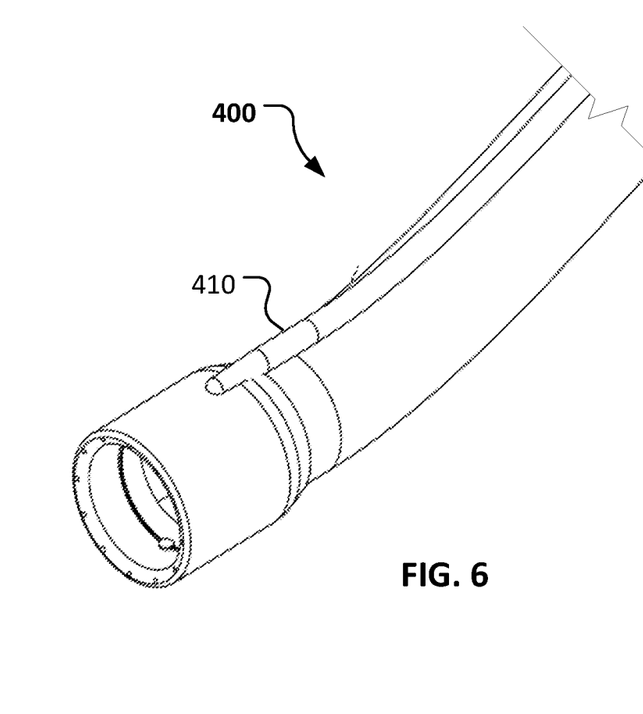

Example system 100 for providing thermal therapy also includes microwave energy system 160. It should be understood that while microwave energy system 160 is depicted in this example embodiment of system 100, in some embodiments other types of energy can be substituted. For example, in some embodiments sources and systems for providing radiofrequency (RF) energy, direct current (DC) energy, cryogenic energy, chemical energy, and the like, can be substituted for microwave energy system 160. In some embodiments, a current-carrying fluid (e.g., saline, hypertonic saline, etc.) is delivered via endoscope apparatus 110 (e.g., through auxiliary channel 310 or 410 as shown in FIGS. 5 and 6) to facilitate enhanced delivery of energy to the target tissue area. The use of a current-carrying fluid can also serve to reduce or minimize the potential for epithelial damage from the energy delivery. Bipolar electrodes or monopolar electrodes can be used to deliver energy in some embodiments.

In some embodiments, the energy source of system 100 can deliver energy on a pulsatile or cyclic basis. In some such embodiments, the frequency of the pulsed energy delivery is adjustable as desired by a clinician operator. For example, a rapid-pulse energy delivery is envisioned within the scope of this disclosure. Such pulsatile energy deliver techniques may allow for advantageous heat dissipation in some implementations. In some embodiments, one or more time-based and/or energy-level-based patterns of energy delivery can be selected by the clinician operator. In some embodiments, the energy source of system 100 can deliver energy on a steady level or continuous level basis. In some embodiments, the energy source of system 100 is configured to deliver energy on a selectable steady level basis, a pattern basis, or a pulsatile basis.

In the depicted embodiment, microwave energy system 160 includes a microwave generator/controller 162, a power meter 164, a system cable 166, a first energy cable 168a, a second energy cable 168b, a first microwave delivery element 170a, and a second microwave delivery element 170b.

While in the depicted embodiment two microwave delivery elements 170a and 170b are included, in some embodiments a single microwave delivery element is included. In some embodiments, three or more microwave delivery elements are included. For example, in some embodiments four, five, six, seven, eight, nine, ten, or more than ten microwave delivery elements are included.

Figure 7:
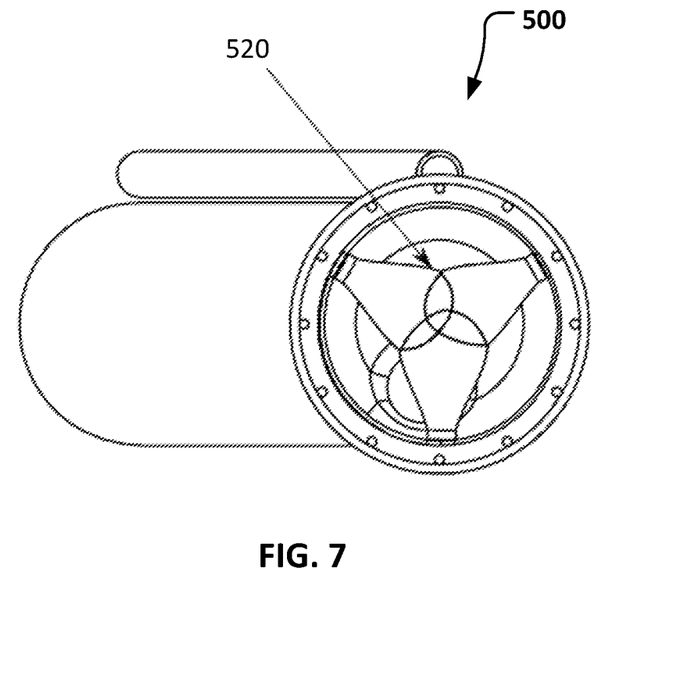
FIG. 7 shows a perspective end view of a distal tip portion of an endoscope that is configured with a cap and three microwave energy delivery elements arranged to create a convergence of energy in the middle region of the cap.

In some embodiments, the microwave delivery elements 170a and 170b may be arranged to create overlapping ablation zones (e.g., see overlapping zone 520 as shown in FIG. 7). An array consisting of multiple microwave delivery elements can create such focused ablation zones (heating in overlapping zones increases exponentially with number of overlapping regions).

In some embodiments, the power supply to each microwave delivery element may be controlled using a phasic system. Energy can be delivered on a phasic basis using multiple microwave delivery elements arranged in an array to focus energy on a discrete location (e.g., at center of cap). This approach ensures that the target location is repeated heated sequentially by microwave delivery elements in the array to maximize ablation in that location while sparing tissue elsewhere. In some embodiments, side firing microwave delivery elements are built into or attached to the cap. In some embodiments, end firing microwave delivery elements are delivered to the cap down working channel(s) of the endoscope.

Still referring to FIG. 1, microwave generator/controller 162 generates the microwave energy that is ultimately delivered to the target tissue area. Microwave generator/controller 162 can be adjustable by the clinician operator. For example, the energy level, energy delivery pattern (e.g., steady, pulsatile, phasic, variable pattern, etc.), timing, and the like can be adjustably controlled.

In some embodiments, temperature feedback is included. In some such embodiments, the temperature of the target tissue area is detected (e.g., using a thermocouple, thermistor, IR detector, etc.) and a signal that is indicative of the temperature is input to microwave generator/controller 162. In such an arrangement, microwave generator/controller 162 can automatically adjust the energy delivery on a closed-loop basis in accordance with selectable parameters.

An analysis of reflected power signal to determine changes in targeted tissue during ablation can be performed in accordance with the devices and methods provided herein. In some embodiments, the reflected power may be detected using a reverse directional coupler. For example, in some embodiments power delivered by the system 100 may be compared to the power reflected to determine amount of power delivered to the target tissue and changes to its dielectric properties caused by the ablation process. Analysis of the rate of change of the reflected power signal may be used to identify a key stage during the ablation process related to the treatment goal.

Power meter 164 provides an indication of the level of energy being delivered from microwave generator/controller 162. In some embodiments, power meter 164 is integral with microwave generator/controller 162. In some embodiments, detection and/or analysis of the reflected power signal may also be used to determine the status of the treatment process. In some embodiments, reflected power may be detected using a reverse direction coupler. The power delivered by the system may be compared to the power reflected to determine the amount of power deliver to the target tissue and changes to its properties caused by the heating process. Analysis of the rate of change of the reflect power signal may be used to identify a key stage or stages during the treatment process.

In the depicted embodiment, two microwave delivery elements 170a and 170b are included. Microwave delivery elements 170a and 170b may also be referred to as antennas. Microwave delivery elements 170a and 170b are electrically communicative with first energy cable 168a and second energy cable 168b respectively. First energy cable 168a and second energy cable 168b can conjoin to form system cable 166 while remaining electrically discrete from each other. System cable 166 is physically and electrically coupled to microwave generator/controller 162. Therefore, microwave energy generated from microwave generator/controller 162 can be transmitted to microwave delivery elements 170a and 170b. The energy may be delivered via the endoscopic or through a cable affixed to the external surface of the endoscope. From microwave delivery elements 170a and 170b, the microwave energy can be delivered to the target tissue such that the desired therapy can be performed.

Figure 2:
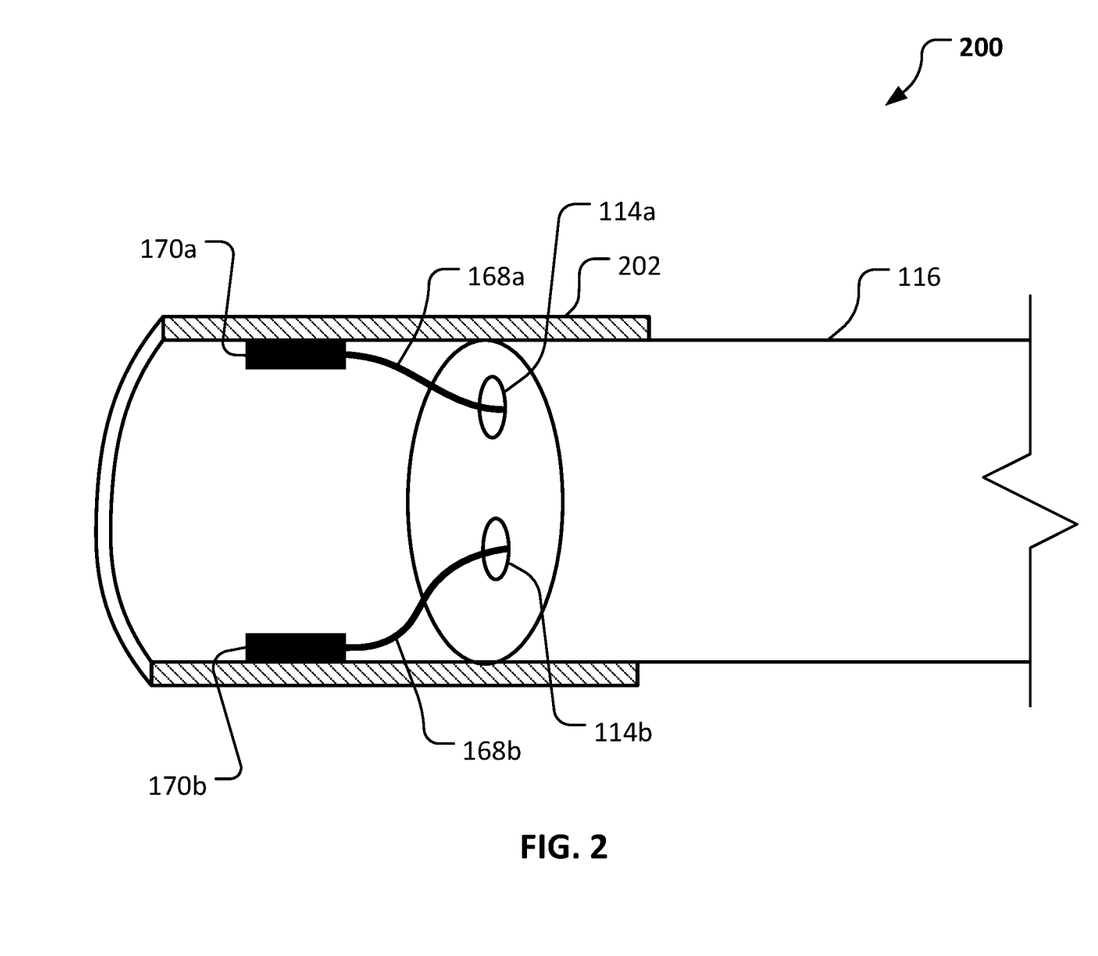
FIG. 2 shows a partial cutaway perspective view of a distal tip portion of an endoscope that is configured with a cap and microwave energy delivery elements, in accordance with some embodiments provided herein.

With reference to FIG. 2, distal end portion 200 of endoscope cable 116 can be releasably coupled with cap assembly 202. In this drawing, cap assembly 202 is shown in cross-section so that the internal region of cap assembly 202 is in view.

In some embodiments, cap assembly 202 is clamped onto distal end portion 200. In some embodiments, other techniques for releasably coupling cap assembly 202 onto distal end portion 200 as used, such as but not limited to, threading, press-fitting, snap-fitting, bayonet style coupling, and the like. In some embodiments, an adapter element is used to releasably couple cap assembly 202 onto distal end portion 200. In some embodiments, cap assembly 202, or a portion of cap assembly 202 may be constructed from an elastomeric material that allows the cap to be stretched to fit onto the endoscope.

In some embodiments, cap assembly 202 is clear or generally transparent. Cap assembly 202 is comprised of a material that is stable when exposed to microwave energy. In some embodiments, cap assembly 202 is made of materials such as, but not limited to, polycarbonate, polyvinylchloride (PVC), polyethylene, polypropylene, polyethersulfone, polyetheretherketone, and other suitable polymeric materials. Cap assembly 202 may include materials for electrical shielding to contain the electrical energy within cap assembly 202.

Cap assembly 202 has microwave delivery elements 170a and 170b releasably attached or fixedly attached thereto. In the depicted embodiment of cap assembly 202, microwave delivery elements 170a and 170b are disposed on opposing locations in relation to each other within cap assembly 202. It should be understood that other arrangements of microwave delivery elements 170a and 170b are also envisioned. For example, in some embodiments a single microwave delivery element is included which can be located on cap assembly 202 or directly on the distal end of endoscope cable 116 or inserted freely through the endoscope channel. In some embodiments, microwave delivery elements 170a and 170b include energy windows. In some embodiments, first energy cable 168a and second energy cable 168b are detachable from microwave delivery elements 170a and 170b, using electrical connectors for example. In some embodiments the energy cable is advanced through the endoscope channel. In some embodiments the energy cable be located outside the endoscope and affixed to its external surface. The energy element may be located within the wall of cap assembly 202 and may include a window to aid the release of energy.

While in the depicted embodiment of endoscope cable 116 only two channels 114a and 114b are shown, it should be understood that one or more other channels are included in some embodiments. The other channels, including an auxiliary channel located externally of the endoscope (e.g., through auxiliary channel 310 or 410 as shown in FIGS. 5 and 6), may be used for purposes such as, but not limited to, suction, wires, irrigation, illumination, visualization, instrument deployment, and the like.

Figure 3:
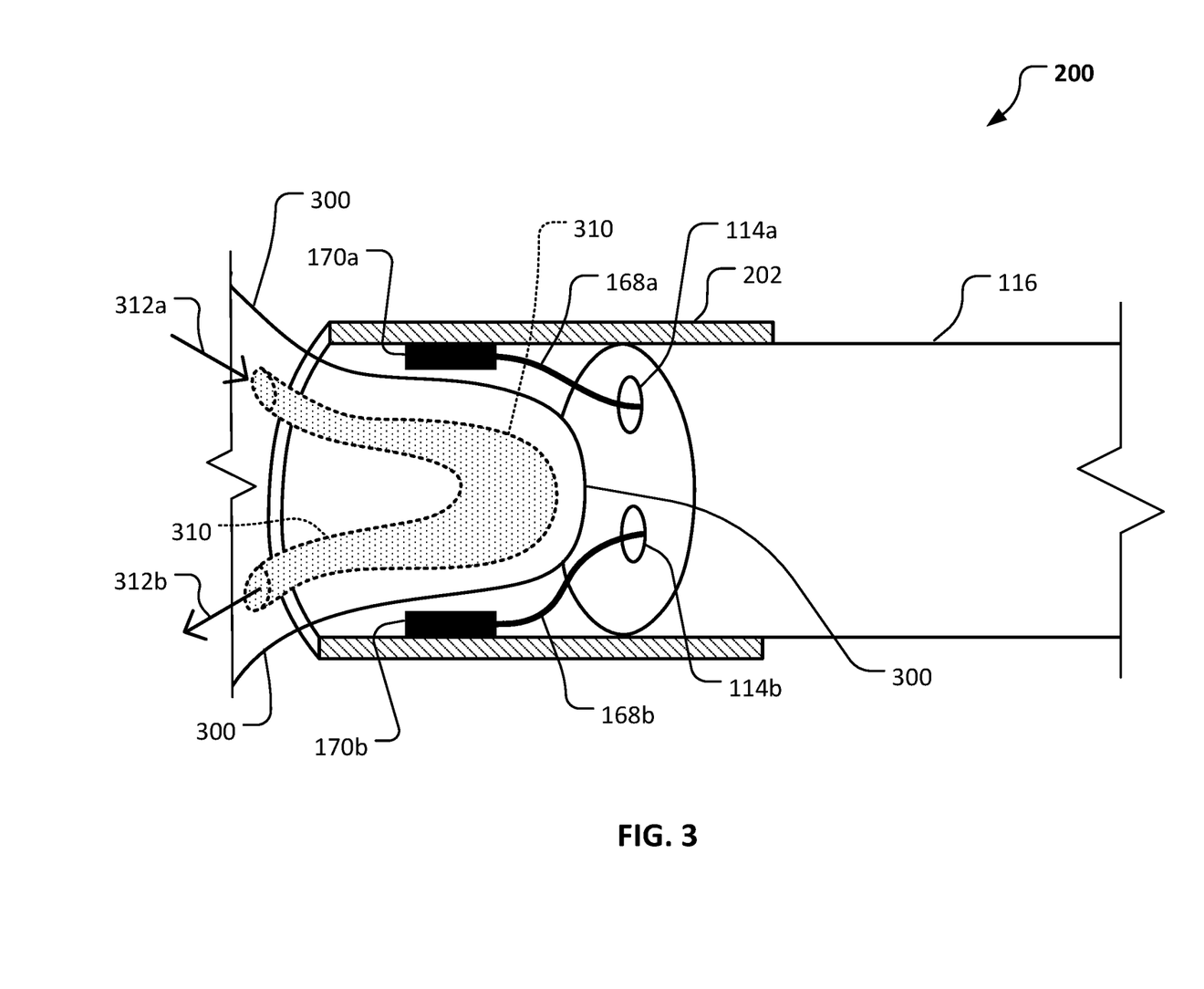
FIG. 3 shows the distal tip portion of FIG. 2 engaging with a varix in preparation for treating the varix, in accordance with some embodiments provided herein.

With reference to FIG. 3, distal end portion 200 and cap assembly 202 of system 100 are shown providing treatment to a blood vessel, i.e., a varix 310. Varix 310 is located within (below) a surface tissue 300 (e.g., mucosa, skin, etc.). In the depicted arrangement, blood is flowing through varix 310 as schematically indicated by arrows 312a and 312b. In some implementations, varix 310 may be an esophageal varix that is located in the lower part of the esophagus of a patient. However, as described elsewhere herein, other treatment applications for system 100, in addition to esophageal varices, are also envisioned within the scope of this disclosure.

In the depicted implementation, suction (e.g., vacuum or negative pressure) is being applied to draw varix 310 within cap assembly 202. Accordingly, varix 310 is positioned generally between microwave delivery elements 170a and 170b.

It should be understood that such suction is not required in all embodiments and implementations of system 100. In some embodiments, no suction is included. In some such embodiments, microwave delivery elements 170a and 170b may be located closer to the distal tip of cap assembly 202. Accordingly, energy from microwave delivery elements 170a and 170b can be thereby delivered to varix 310 without drawing varix 310 within the interior space of cap assembly 202. In some such embodiments, a single microwave delivery element is included.

Other methods for facilitating contact between the cap assembly 202 and the target anatomy (e.g., varix 310) can be additionally or alternatively used. For example, in some implementations cryoenergy is delivered before and/or generally simultaneously along with the delivery of the microwave or other high-frequency energy. The cryoenergy serves to cause adhesion of the cap assembly 202 and/or microwave delivery elements 170a and 170b to the tissue of interest (e.g., blood vessel, bleeding varices, or tumor). With the adhesion contact established, the microwave or other energy can be delivered efficiently to the target tissue. In doing so, there may be eventual loss of adhesion as the contact caused by the cryoenergy abates, but inherently such a technique will advantageously cause less heating on the tissue surface, thus treating the tissue of interest without significant endothelial damage.

Alternatively or additionally, in some implementations another beneficial technique is to initially use radiofrequency energy and a power-control titration mode with no temperature cutoff. This will cause rapid coagulum formation and get contact to the desired site for microwave or other energy delivery.

In the configuration shown, energy can be delivered by microwave delivery elements 170a and 170b and received by varix 310. In some embodiments, the microwave energy may be delivered at frequencies, for example, in the range of about 300 MHz to about 300 GHz, or about 800 MHz to 8 GHz, or about 1 GHz to 6 GHz. It should be understood that other types of high-frequency electromagnetic energy instead of, or in addition to, microwave energy can be delivered in some implementations of system 100. It should also be understood that such energy delivery therapy can be performed so that epithelial damage and coagulation within varix 310 result, while not inflicting substantial damage to surface tissue 300. In some embodiments, the power of the microwave energy may be in the range, for example, of about 10 watts to about 900 watts, or about 20 watts to about 150 watts, or about 100 watts to about 300 watts. The duration of the microwave energy may be in the range, for example, of about 10 milliseconds to about 30 minutes, or about 10 seconds to about 30 seconds, or about 5 seconds to about 20 seconds.

In some implementations, elements 170a and 170b can be used in coordination with each other to facilitate phase and wave summation, thereby creating maximum impedance changes deeper in the tissue. Because the tissue impedance change results in resistive heating, the site of heating will therefore be manipulatable, modulatable, and targeted away from the endothelial surface, when using such a phase and wave summation technique.

Additional systems and techniques for the titration and control of the energy level delivered can be utilized in conjunction with system 100 in some implementations. Such detection and feedback systems can help to facilitate avoidance of adverse effects such as over-ablation and sloughing of tissue.

In some implementations, a Doppler probe system (not shown) is advantageously used in conjunction with system 100 to provide energy titration (modulation). For example, the Doppler probe can be used to detect the velocity of blood flowing through varix 310, and to provide feedback that can be used for controlling the energy level being delivered. Such a feedback system can help to avoid over-ablation and sloughing of tissue.

Initially, before the delivery of the energy, the Doppler probe can be used to measure a baseline flow rate of blood through varix 310. While the energy is being delivered to varix 310, the Doppler probe can continue detecting the blood flow through varix 310. As coagulation begins, the blood flow through varix 310 will decrease. Such a decrease in blood flow will be detected by the Doppler probe, and a feedback signal indicative of the detected blood flow can be provided from the Doppler probe system to the energy control system (e.g., microwave generator/controller 162). In some embodiments, the energy control system can be programmed to modulate the energy delivery intensity in response to the signal from the Doppler probe system. As the blood flow reduces to approximately zero, the energy delivered can be ceased. Accordingly, the Doppler probe can be used in a closed-loop or partially closed-loop arrangement to help to avoid over-ablation and sloughing of tissue.

In a related implementation for tumor ablation or superficial cancer ablation, a reverse-type of titration using a Doppler probe system can be used. In other words, the Doppler probe system can detect and identify low-flow areas that can then be targeted for ablation so as to avoid significant collateral damage.

Alternatively or additionally, in some implementations for treating varices, titration of the microwave power or other energy source energy delivered can be based on impedance. For example, in some implementations power delivery would start at 20 W and be automatically titrated up until the impedance falls by a particular amount (e.g., 10 to 15 ohms in some implementations). Such an impedance fall is anticipated because of extracellular fluid and extravasation from energy-related cell death. The power being delivered will be titrated down if the impedance increases further (suggesting coagulum or char or endothelial damage), or titrated up if the impedance fall is insufficient.

Alternatively or additionally, in some implementations for treating varices or other conditions, titration of the microwave power or other energy source energy delivered can be based on measured temperature and temperature differential feedback. For example, a first thermistor can be located on the endoscope probe itself, a second thermistor or thermocouple can be located on the energy delivery electrode, and a third thermistor can be located on the internal surface of the endoscope more proximally. The temperature gradient between these three temperature sensors will be used to titrate energy delivery at the specific site of interest, again helping to minimize the potential for collateral damage.

Figure 4:
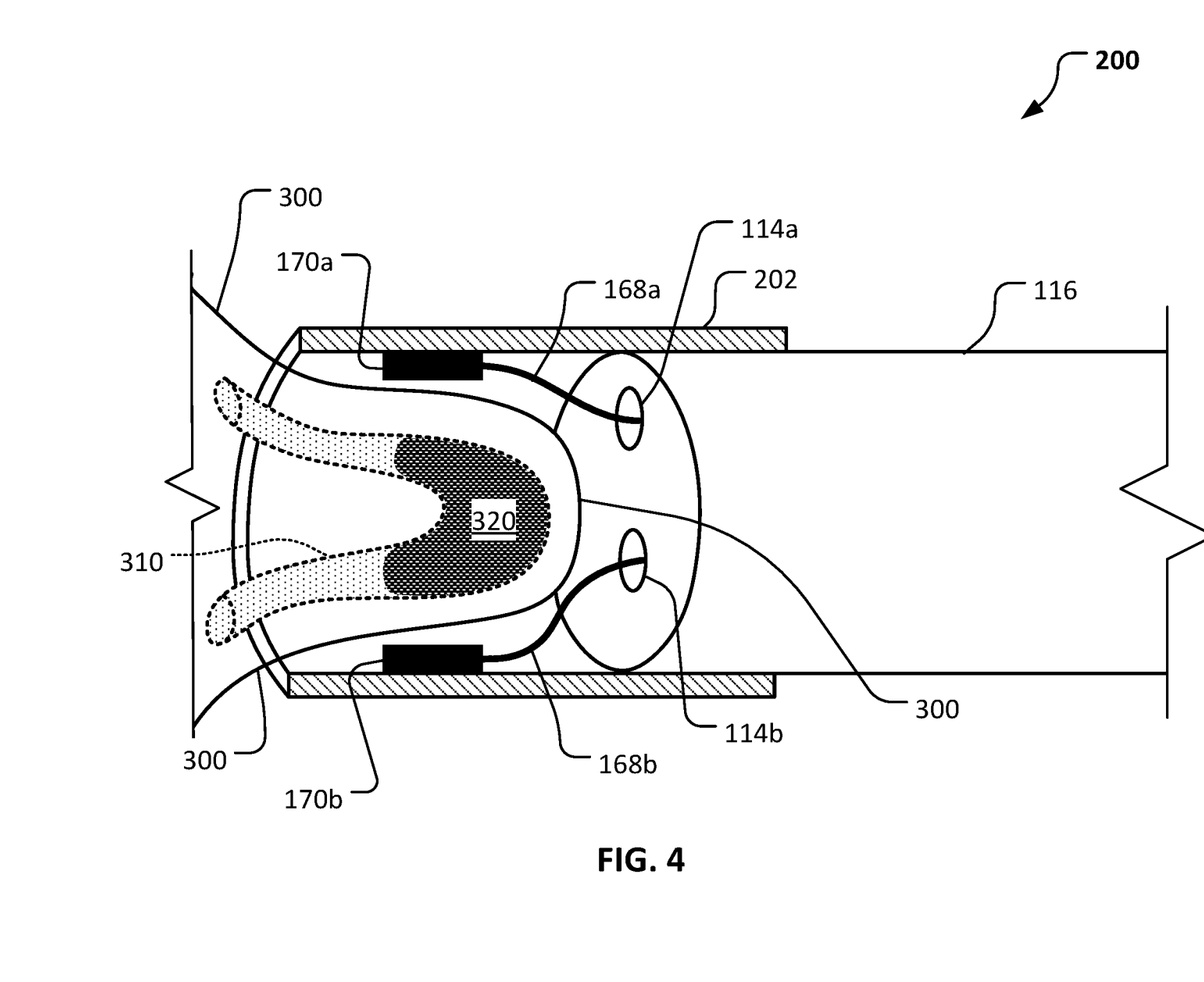
FIG. 4 shows the arrangement of FIG. 3 after the varix has been treated to cause coagulation of the varix, in accordance with some embodiments provided herein.

With reference to FIG. 4, energy delivered by microwave delivery elements 170a and 170b and received by varix 310 can cause blood coagulation resulting in the formation of an intended thrombus 320. As a result, essentially no blood is flowing through varix 310. As such, the potential for varix 310 to leak blood or to rupture, causing life-threatening bleeding, is reduced or eliminated.

In some implementations of system 100, multidirectional thermal therapy that does not injure surface tissue 300 but causes endothelial injury and coagulation to a target vessel such as varix 310 is delivered. In some such embodiments, Doppler modulation of microwave energy can direct heat in sub-mucosal tissue to cause rapid coagulation and eventual obliteration of varix 310 without tissue surface 300 injury. Surface cooling by the delivery of cooling fluid to the tissue surface 300 via endoscope ports or supplied via an auxiliary channel (e.g., through auxiliary channel 310 or 410 as shown in FIGS. 5 and 6) may optionally be included to further reduce the potential of tissue surface injury.

Alternatively, or additionally, the cap assembly 202 and/or other portions of the endoscope 116 can be cooled, resulting in cooling of the tissue surface 300. Accordingly, power delivery will be focused at deeper sites. The feeding blood vessel for a varix or a tumor can thereby be ablated, with little or no effect on the surface 300.

Figure 8:
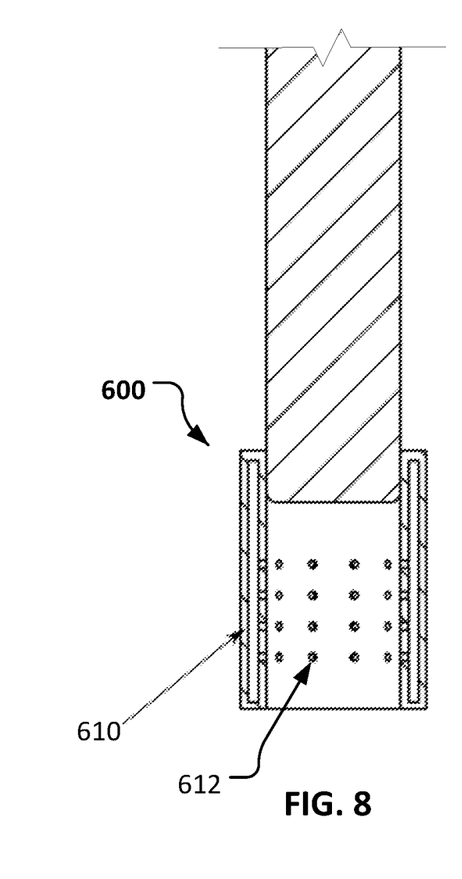
FIG. 8 is a longitudinal cross-sectional view of a distal tip portion of an endoscope that is configured with a cap and microwave energy delivery elements, and that includes cooling fluid channels and apertures.

Also referring to FIG. 8, in some embodiments a cooling fluid (e.g., water, etc.) may be circulated through channels 610 within the wall of a cap 600. In some embodiments, cooling fluid may be emitted through a number of ports 612 within the cap 600 to cool the tissue receiving the thermal treatment. Ports 612 may create cooling fluid sprays integrated into cap 600 to evenly cool the surface layer of tissue suctioned into the cap 600.

It should be understood that one or more of the features described in reference to a particular embodiment can be combined with one or more features described in reference to another embodiment. Hence, features can be combined to create hybrid designs, and such designs are within the scope of this disclosure.

Another technique that can be used in some implementations to further reduce the potential for unwanted tissue injury is phasic microwave energy delivery. Phasic delivery allows cooling of deeper structures in addition to other techniques described above for cooling more superficially. In some embodiments energy may be delivered via a number of energy delivery elements arranged in a circular array and triggered using a phasic control system. In some embodiments using this configuration a discrete portion located within the cap is repeated targeted by each delivery element arranged in a circular array. Accordingly, phasic energy delivery can be used to help avoid perforation or damage to surface tissue layers. That is the case because the phased delivery allows for deeper vessel-related cooling of the deepest structures before the next burst or phase of delivery is done. Using a temperature sensing method as described above, temperature gradients can be visually displayed and then used to automate the characteristics of the phasic current, including amplitude, pulse width, and time between phase pulse deliveries. Similar a measurement of reflected power may be used to monitor and control the treatment process and identify when the treatment process is complete.

In another related therapeutic technique, microwave energy delivery, such as described above, can also be used to deliver or change/cure chemicals and biologicals that can be eluted from the surface of the probe or endoscope. For example, such techniques can be used with cell adhesion molecules to treat desquamating disorders anywhere in the GI tract, or portion to include regenerative therapy so as to replenish the endothelium following an ablative or tumor therapy session. The beneficial use of the interactions between the energy delivery and the ability to deliver chemical and biological agents, as well as to change the chemical characteristics of such agents with the energy delivery, is also envisioned within the scope of this disclosure.

Figures 9, 10:
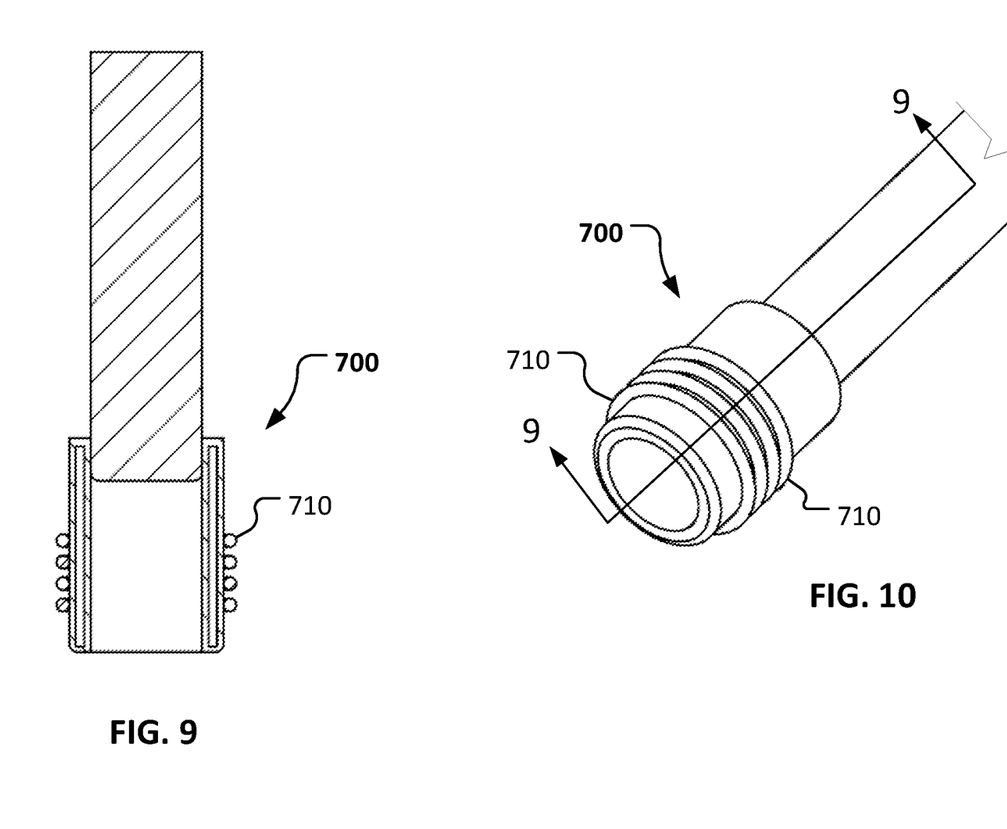
FIG. 9 is a longitudinal cross-sectional view of a distal tip portion of an endoscope that is configured with a cap and microwave energy delivery elements, and that includes ligation bands mounted to the outside of the cap.
FIG. 10 is a perspective view of the distal tip portion of FIG. 9.

Referring to FIGS. 9 and 10, in some embodiments one or more ligation bands 710 may be mounted to the external surface of a cap 700. One or more ligation bands 710 may be applied to the tissue receiving thermal treatment, i.e., to ligate the tissue. The ligate system may be used in combination with the thermal treatment supplied using the microwave energy source. In one embodiment the effector device may be an elastic ring deployed remotely after tissue has been suctioned in the cap during the treatment.

In another embodiment treatment may be delivered via a paddle instead of a cap where tissue is suctioned into a recess on the paddle and one or more energy delivery elements are used to deliver treatment. The paddle may be supplied with a vacuum source to capture the tissue and a cooling fluid to spare tissue during therapy delivery. The paddle may be attached to the endoscope use the endoscope channel or an auxiliary channel to supply electrical energy, vacuum or cooling fluid.

In some embodiments, the cable(s) for the endoscope is disposable. In some embodiments, the cable(s) for the endoscope is reusable.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An apparatus for minimally invasive delivery of therapeutic energy to a target area tissue of a patient, the apparatus comprising:
    a cap assembly defining an interior space configured to receive the target area tissue, the cap assembly configured to be releasably coupled to a distal end portion of an endoscope, the cap assembly defining one or more cooling fluid channels and a plurality of openings fluidly coupling the one or more cooling fluid channels to the interior space;
    an energy source; and
    at least one energy delivery element, the at least one energy delivery element coupled to the cap assembly, the at least one energy delivery element configured to receive energy from the energy source and to deliver the energy to the target area tissue.

2. The apparatus of claim 1, wherein the at least one energy delivery element is releasably coupled to the cap assembly.

3. The apparatus of claim 1, wherein the energy source is a microwave energy source.

4. The apparatus of claim 1, further comprising a temperature sensor, the temperature sensor configured to detect a temperature of the target area and to provide a signal indicative of the temperature to the energy source.

5. A system for minimally invasive delivery of therapeutic energy to a target area of a patient, the system comprising:
    a Doppler probe configured to detect a velocity of blood flow within a vessel;
    an endoscope;
    a cap assembly, the cap assembly being releasably couple-able to a distal end portion of the endoscope;
    an energy source configured to generate energy and to modulate a level of the energy in response to the velocity of blood flow detected by the Doppler probe; and
    at least one energy delivery element, the at least one energy delivery element coupled to the cap assembly, the at least one energy delivery element configured to receive the energy from the energy source and to deliver the energy to the target area.

6. The system of claim 5, wherein the at least one energy delivery element is releasably coupled to the cap assembly.

7. The system of claim 5, wherein the energy source is a microwave energy source.

8. The system of claim 5, further comprising a temperature sensor, the temperature sensor configured to detect a temperature of the target area and to provide a signal indicative of the temperature to the energy source.

9. The system of claim 5, wherein the endoscope is configured to deliver at least one of suction and an irrigation fluid to the target area.

* * * * *